(12) United States Patent
Mano et al.

(10) Patent No.: US 6,500,943 B2
(45) Date of Patent: Dec. 31, 2002

(54) PROMOTER

(75) Inventors: Hiroyuki Mano, Utsunomiya (JP); Tsuneaki Sakata, Toyonaka (JP); Mamoru Hasegawa, Tsukuba (JP); Toshiaki Tabata, Tsukuba (JP)

(73) Assignee: Dnavec Research Inc., Ibaraki (JP)

( * ) Notice: Subject to any disclaimer, the term of this patent is extended or adjusted under 35 U.S.C. 154(b) by 0 days.

(21) Appl. No.: 10/045,428

(22) Filed: Nov. 8, 2001

(65) Prior Publication Data

US 2002/0115845 A1 Aug. 22, 2002

Related U.S. Application Data

(63) Continuation-in-part of application No. 09/735,103, filed on Dec. 12, 2000, now abandoned, which is a continuation-in-part of application No. 09/142,529, filed as application No. PCT/JP97/00741 on Mar. 10, 1997, now Pat. No. 6,225,459.

(30) Foreign Application Priority Data

Mar. 12, 1996 (JP) ................................. 8-54294

(51) Int. Cl.$^7$ ......................... C07H 21/04; C12N 15/63; C12N 15/85; C12N 1/20; C12N 15/00
(52) U.S. Cl. .................. 536/24.1; 536/23.1; 435/320.1; 435/325; 435/252.3
(58) Field of Search .............................. 435/320.1, 325, 435/252.3; 536/23.1, 24.1

(56) References Cited

U.S. PATENT DOCUMENTS 6,225,459 B1 * 5/2001 Mano et al. ................ 536/24.1

OTHER PUBLICATIONS

Birren et al., "Homo sapiens Chromosome 4, Clone RP11–793H20," GenBank Accession No. AC036224 (2000).

Dzierzak et al., "Lineage–Specific Expression of a Human β–globin Gene in Murine Bone Marrow Transplant Recipients Reconstituted with Retrovirus–Transduced Stem Cells," *Nature* 331:35–41 (1988).

Honda et al., "Cloning and Characterization of Mouse tec Promoter," *Biochemical and Biophysical Research Communications* 223:422–426 (1996).

Ido et al., "Gene Therapy for Hepatoma Cells Using a Retrovirus Vector Carrying Herpes Simplex Virus Thymidine Kinase Gene under the Control of Human α–Fetoprotein Gene Promoter," *Cancer Research* 55:3105–3109 (1995).

Mano et al., "A Novel Protein–Tyrosine Kinase, tec, Is Preferentially Expressed in Liver," *Oncogene* 5:1781–1786 (1990).

Mano et al., "Expression of a Novel Form of tec Kinase in Hematopoietic Cells and Mapping of the Gene to Chromosome 5 Near kit," *Oncogene* 8:417–424 (1993).

\* cited by examiner

*Primary Examiner*—David Guzo
*Assistant Examiner*—Gerald G. Leffers, Jr.
(74) *Attorney, Agent, or Firm*—Clark & Elbing LLP

(57) ABSTRACT

The present invention provides a DNA having promoter activity of Tec tyrosine kinase and a vector having incorporated within it the promoter to thereby enable a high level expression of an exogenous gene in hematopoietic stem cells and hepatic cells.

3 Claims, 7 Drawing Sheets

FIG. 1

```
AGCTTGTCAG TAAGCCACCA TTCTTCTATC ACCCCAGAGC ACAGCATCAT CGGTTTTCAC   60
CCGCGAGGGG CTAAGCGGAA GTGGAGGTCG GTTCTTAGCC ACCCACAAGT GCTATTGCTA  120
CGTCCTCCGA GCCGGGGATC GAAGGAGCAT TTTTCTGGAC GGTTCTCTTA GGATGGGAAG  180
TCCGGACTTA GAGAGACCCC ACGCCGCGTC TGTCTGGATA AGAGACGCTC CCTGGAACTT  240
                                       GATA
CGGCCGCAGG ACCGAGAGCT CCGATTCTTC CCTTTGGCTT TGAAATCGCG GAAGGAAGGT  300
GGGACACTGG CGCTCTGGGC ACGAGGCAGA GCGACGCCGAG GGCGGGCCAG GAGAGCCGGG  360
                                                           SP-1
CGGTGGGCGT GGCGATGGGT TTGGTCAGCG CTTGCCGAGC TCCGGGCTCC GCAGTTTGGA  420
                                           SP-1   → ←
CGTCGCTCTG TCTTGGCTTC TCTCGGCACG CGCTCCGTCA AGTAAGAAC CAAGGGACTC  480
```

FIG. 3A ctagaactgcatataagtcctgccccatttatcctttgggccttccaaaagtctgccttccatttgtttacaatgtatgctcactgtgttgggaa ctacatgtctacacatggcccgttatgagagcatcgtgctcttccctggtatccattcttgtgttttttcagacgagtctgctctgt cgcccaggctggagtgcagtggcgatcttggctcactgcaagctctctgccctcctgggttcatgcgattcctgcctcagctcccgagtagctgg gactacaggcccccgccaccagcctgctaattttttgtattttttagtagagacggggtttcaccgtgttagccaggatgatctttgatctcctga cctcgtgatccgcctgcctgtcggccctcccaaagtgctgggattacaggcgtgagccaccgtgcccggcctctgtcttataagtagtcatttcaccc ttgaaatgtgttgcacaagatgaaatataatttccagagaaatgtatttgcattctgacagtttcttaggaaagaaggatggagtgccaaaat tttaatatggaataaggaagaccaactagatgcaaaaaggcaagagctttcctgtgactcctagcttaagttgcttgttggttaattagttct gtggtttagctgctactgagagctgtagacactgggactggataaagagagttcagtgtctccttaagatagtggctctcaat tctatcagtacagaaatcatgatgctcagggctcctcccagaccaactgaataaaaaaacctgaatgaagctagacatctgtattaaaatga aattccctagattctaatacacacttaagttgagaaccattccttaacagcagttggaaggctttaattaataggagccattaggagagactacatcaagg agaatatgattagctctatgatgatgatagaaattatgcccaggagttggaaggctttaattaataggagccattaggagagactacatcaagg aggggaatttgagctgtgtatctttcacagtggaaagcagagagtccactaggcagggaatgaatgctgtgaggggaatctccggagattggaa agactattttgattggtgtggggaggcattcaggattctgatgagtaaagatgactaggctgcagccagagtctctgtcagactaaggaattttagc tttactctgcaggtcgtggggaggcattcaggattctgatgagtaaagatgactaggctgcagccagagtctctgtcagactaaggaattttagc gcagtttgaataaagcaggcaagaacttgaggaaatgaagaccaattggaagctactctcatggtccagatgtggggtcataatgttctgagcga ggcaaatagccgtggaattaaaatgataaacatttgcgtagtatttcatgtcagttcttgccatatctcattaaacctcacactgaccttgt

FIG. 3B

```
ggtctttcttccatacttacaaatgaaggaactgatgttcagagagaagctgttgtaaaggaacttatagaaaatgaagggcctgattggatg
atgaccaatcagtaataggaaattaaaggtgcattggagtgttgattgggtgttgaagatgtagaattcctcagtgctaaccgtgtccagtca
ccggccgtgctgtctgagagccacttcatgctgttcatgtgactctcttgcctctgtccttaatatgcagtatttattattattattattatt
attattattgagacggagtttcgctctgtcgttgcccaggctgaagtgcaatggtgcgatctcggctcactgaaactccactcccagttcaagcga
ttctcctgcctcagcctcccgagtactgggattacaggcacctgccaccatgtccagctaatttttgtatttttagtagagacggggtttcacca
tgttggcaggctgtctcaaactcgtgacctcaggtgatccacctgcctcggcctcccaaagtgctggattacaggcgtgagccaccacgctcag
cctattattattttttgagacgaagtcttgctctgtcacccaggctggagtgcagtggtgctgtctgctcactgcacctccccagt
tcaagtgattctctgcctcagcctcctgagtagctgggattacaggcatgccagctaatttttgtatttagtaaagatgagt
tttgctatgttggccaggctgctctcttgaactcctcacctaaagtgatctgcccaaagtgctgggattaacaggcgtgagccactgcccagccacag
ttacttctttaaaggcatagtggaggcaagagaagagaggctgtgttaattcaactgtctcaaatatgaatagtctggagttgaatctttttgaatgtct
ttgggttttcagatagtaattgttgaattttaaaaggctcagtctagtatgaatagtctggagacaggagcataggagaagagaactctgagcatgta
ggactctgccctgagcaggttaactatgactggtagtttccatttctcttgtgtgagacaggagcataggagaagagaactctgagcatgta
gtgtagacacagagaacatcctgtggcactgttcattgagattacttcattgagatgcttcattgagattacatcttatcagagctgagtatgaatcatatccacca
ccatgctaattcattgttcatgagtgctgtgtctgaaggtcatctgttttgtgaaccagatcctgaagcaattcaaatgccagtgaaatc
agccacacaggtgacgaaatgtctttcatatgagatactgttccctgcaatcaaatagtaggagtgcaccagaaagctaagggtactaggagg
taaaaggaatgaatcatcatgaagaacttgattagattttctcatgaaatgatgagatgtggaggagcaggatgaaactgaaaggaga
ggagattgaattttgtgcccagg
```

FIG. 4

[Primer list]

F1-primer   5'-ggggtacccctagaactgcatataagtcctgccc-3'

F2-primer   5'-ggggtacccgaaattatgcccaggagttggaag-3'

F3-primer   5'-ggggtaccccaattttttgtattttagtagagac-3'

R1-primer   5'-gaagatcttctatcactcatcatagagctaatcat-3'

R2-primer   5'-gaagatcttcaattagctggacatggtggcaggt-3'

R3-primer   5'-gaagatcttccctggggcacaaaaattcaatctcc-3'

[Primer set]

Fragment1---F1 and R1 (1021bp)

Fragment2---F1 and R2 (2025bp)

Fragment3---F1 and R3 (3150bp)

Fragment4---F2 and R2 (1026bp)

Fragment5---F2 and R3 (2151bp)

Fragment6---F3 and R3 (1151bp)

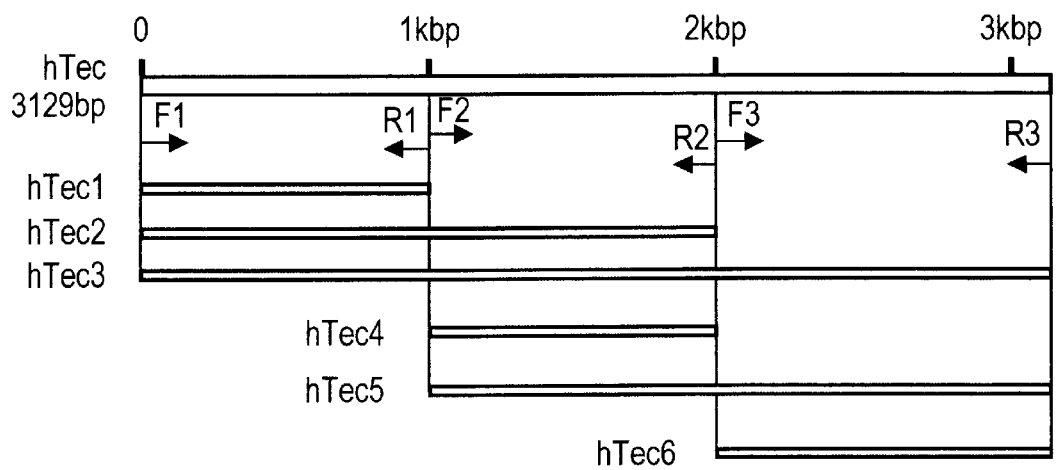

Ba/F3 cell

|  | FF luci | RL luci | FF/RL |
|---|---|---|---|
| PC | 720964 | 75361 | 9.57 |
| NC | 14476 | 78929 | 0.18 |
| mouse Tec | 386874 | 69347 | 5.58 |
| hTec1 | 522 | 57165 | 0.0091 |
| hTec2 | 2776 | 46621 | 0.0595 |
| hTec3 | 427 | 56198 | 0.0076 |
| hTec4 | 5121 | 55991 | 0.0915 |
| hTec5 | 373 | 55262 | 0.0067 |
| hTec6 | 371 | 58829 | 0.0063 |

293T cell

| | FF luci | RL luci | FF/RL |
|---|---|---|---|
| PC | 44914432 | 58485304 | 0.767 |
| NC | 27146144 | 56997944 | 0.476 |
| mouse Tec | 11892524 | 55008904 | 0.216 |
| hTec1 | 1943245 | 54406064 | 0.036 |
| hTec2 | 38888932 | 54440220 | 0.714 |
| hTec3 | 3939613 | 53678020 | 0.073 |
| hTec4 | 52049640 | 57235076 | 0.909 |
| hTec5 | 3177052 | 53319496 | 0.059 |
| hTec6 | 2495796 | 54542436 | 0.045 |

SEQUENCE LISTING

```
<160> NUMBER OF SEQ ID NOS: 16

<210> SEQ ID NO 1
<211> LENGTH: 480
<212> TYPE: DNA
<213> ORGANISM: Mus musculus

<400> SEQUENCE: 1
agcttgtcag taagccacca ttcttctatc accccagagc acagcatcat cggttttcac      60
ccgcgagggg ctaagcggaa gtggaggtcg gttcttagcc acccacaagt gctattgcta     120
cgtcctccga gccggggatc gaaggagcat ttttctggac ggttctctta ggatgggaag     180
tccggactta gagagacccc acgccgcgtc tgtctggata agagacgctc cctggaactt     240
cggccgcagg accgagagct ccgattcttc cctttggctt tgaaatcgcg gaaggaaggt     300
gggacactgg cgctctgggc acgaggcaga gcgacgcgag ggcgggccag gagagccggg     360
cggtgggcgt ggcgatgggt ttggtcagcg cttgccgagc tccgggctcc gcagtttgga     420
cgtcgctctg tctttggcttg tctcggcacg cgctccgtca aggtaagaac caagggactc     480
```

<210> SEQ ID NO 2
<211> LENGTH: 2574
<212> TYPE: DNA
<213> ORGANISM: Mus musculus

<400> SEQUENCE: 2

| | | | | | |
|---|---|---|---|---|---|
| gagctccggc | ctccgcagtt | tggacgtcgc | tctgtcttgg | cttgtctcgg | cacgcgctcc | 60 |
| gtcaagaatc | cggagatcgt | caatggctgg | agaaagagca | accagaagac | cgagatgaat | 120 |
| ttcaacacta | tcctagaaga | gattcttatt | aaaaggtccc | agcagaaaaa | gaagacatca | 180 |
| ctcttaaact | acaaagagag | actttgtgta | cttccaaaat | ccgtgttgag | ctactatgag | 240 |
| ggtcgagcgg | agaagaaata | cagaaagggc | gtcattgata | tttccaaaat | caagtgtgtg | 300 |
| gagatagtga | agaacgatga | tggtgtcatt | ccctgtcaaa | ataaatttcc | attccaggtt | 360 |
| gttcatgatg | ctaatacact | ttatattttt | gcacctagtc | cacaaagcag | ggaccgatgg | 420 |
| gtgaagaagt | taaagaaga | aataaagaac | aacaataata | tcatgattaa | ataccatcct | 480 |
| aaattctggg | cagatgggag | ttaccagtgt | tgtagacaaa | cagaaaaact | agcacccgga | 540 |
| tgtgagaagt | acaatctttt | tgagagtagt | ataagaaaga | ccctgcctcc | cgcgccagaa | 600 |
| ataaagaaga | gaaggcctcc | tccaccaatt | ccccagagg | aagaaaatac | tgaagaaatc | 660 |
| gttgtagcga | tgtatgactt | ccaagcgacg | gaagcacatg | acctcaggtt | agagagaggc | 720 |
| caagagtata | tcatcctgga | aaagaatgac | ctccattggt | ggagagcgag | agataagtat | 780 |
| gggagtgaag | gatatatccc | aagtaattac | gtcacaggga | agaaatccaa | caacttagat | 840 |
| caatatgagt | ggtactgcag | aaataccaac | agaagcaaag | cagaacagct | cctcagaacg | 900 |
| gaagataaag | aaggtggttt | tatggtgaga | gactccagtc | aaccaggctt | gtacactgtc | 960 |
| tccctttaca | caaagtttgg | gggagaaggc | tcatcaggtt | tcaggcatta | tcacataaag | 1020 |
| gaaacagcaa | catccccaaa | gaagtattac | ctggcagaga | agcatgcttt | cgggtccatt | 1080 |
| cctgagatca | ttgaatatca | caagcacaat | gcggcagggc | ttgtcaccag | gctgcggtac | 1140 |
| ccggtcagta | caaaggggaa | gaacgctccc | actactgcgg | ccttcagcta | tgataagtgg | 1200 |
| gagattaacc | catcagagct | gacctttatg | agagagttgg | ggagcggact | gtttggagtg | 1260 |
| gtgaggcttg | gcaagtggcg | ggcccagtac | aaagtggcca | tcaaagctat | ccgggaaggc | 1320 |
| gccatgtgtg | aagaggattt | catagaggaa | gctaaagtca | tgatgaagct | gacacacccc | 1380 |
| aagctggtac | agctctatgg | tgtatgcacc | cagcagaagc | ccatctacat | cgttaccgag | 1440 |
| ttcatggaac | ggggctgcct | tctgaatttc | ctccggcaga | gacaaggcca | tttcagcaga | 1500 |
| gacatgctgc | taagcatgtg | tcaagatgtc | tgtgaaggga | tggagtacct | ggagagaaac | 1560 |
| ttcttcatcc | acagagacct | ggctgccaga | aattgtctag | tgaatgaagc | aggagttgtc | 1620 |
| aaagtatctg | attttggaat | ggccaggtac | gttctggatg | atcagtacac | aagttcttct | 1680 |
| tgcgccaagt | tccctgtgaa | gtggtgtccc | ccagaagtgt | taattacag | ccgctttagc | 1740 |
| agcaagtcag | acgtctggtc | gtttggtgtg | ctaatgtggg | aaatattcac | agaaggcagg | 1800 |
| atgcccttg | agaagaacac | caattacgaa | gtggtaacca | tggtgactcg | tggccaccgc | 1860 |
| ctccaccggc | caaagctggc | ttccaaatat | ttgtatgagg | tgatgctgag | atgctggcaa | 1920 |
| gagagaccag | agggaaggcc | ttcctttgaa | gacttgctgc | gtacgataga | tgaactagtt | 1980 |
| gaatgtgaag | aaactttgg | aagatgaatg | gtggtcccag | tttccaaggc | aagaggaaga | 2040 |
| aatggtgtgc | catcggaacg | caattctctt | ggcacctggg | agtatagact | gctctgctta | 2100 |

```
caacacggta gccccagctc atctgctgct gatccagcct gagctcagtc cctgctttgc    2160
cggctgcaca gatggtctct cagagctggt gacgtgaagc actgattttg ctcatttctt    2220
caagggtttg agtgccagcc atgtatacca ggctctgtgc ccaggcctca ggagatgaac    2280
atgggactat gctagctgat gctagcggaa agccagggtg gttgtgatgg ggacgagtca    2340
tgtcccagcg tctcttccat gcccttggc tattacataa acctgggcct ggagtgttgt    2400
ctaccactga gttctaggaa aagcaggaac ccacctggat acgtagtaat cctctgtttt    2460
ggaaacatct ctttccaaac ttgttcttag tagtatgctt aaaaatttgt atattgtata    2520
tattgtaaat acatataata tataaagtta tatatttata agtaaaaaaa aaaa          2574

<210> SEQ ID NO 3
<211> LENGTH: 17
<212> TYPE: DNA
<213> ORGANISM: Artificial Sequence
<220> FEATURE:
<223> OTHER INFORMATION: Probe/primer derived from Mus musculus.

<400> SEQUENCE: 3
ttagcatcat gaacaac                                                   17

<210> SEQ ID NO 4
<211> LENGTH: 21
<212> TYPE: DNA
<213> ORGANISM: Artificial Sequence
<220> FEATURE:
<223> OTHER INFORMATION: Probe/primer derived from Mus musculus.

<400> SEQUENCE: 4
ccttaccctc atagtagctc a                                              21

<210> SEQ ID NO 5
<211> LENGTH: 35
<212> TYPE: DNA
<213> ORGANISM: Artificial Sequence
<220> FEATURE:
<223> OTHER INFORMATION: Probe/primer derived from Mus musculus.

<400> SEQUENCE: 5
gactcgagtc gacatcgatt tttttttttt ttttt                               35

<210> SEQ ID NO 6
<211> LENGTH: 20
<212> TYPE: DNA
<213> ORGANISM: Artificial Sequence
<220> FEATURE:
<223> OTHER INFORMATION: Probe/primer derived from Mus musculus.

<400> SEQUENCE: 6
tcaacactat cctagaagag                                                20

<210> SEQ ID NO 7
<211> LENGTH: 17
<212> TYPE: DNA
<213> ORGANISM: Artificial Sequence
<220> FEATURE:
<223> OTHER INFORMATION: Probe/primer derived from Mus musculus.

<400> SEQUENCE: 7
gactcgagtc gacatcg                                                   17

<210> SEQ ID NO 8
<211> LENGTH: 25
```

```
<212> TYPE: DNA
<213> ORGANISM: Artificial Sequence
<220> FEATURE:
<223> OTHER INFORMATION: Probe/primer derived from Mus musculus.

<400> SEQUENCE: 8
gcagtttgga cgtcgctctg tcttg                                          25

<210> SEQ ID NO 9
<211> LENGTH: 3129
<212> TYPE: DNA
<213> ORGANISM: Homo sapiens

<400> SEQUENCE: 9
ctagaactgc atataagtcc tgccccattt atcctttggg ccttccaaaa gtctgccttc    60
catttgttta caatggtatt gctcactgtg ttgggaacta catgtctaca catggcccgt   120
ttatgagagc atcgcttgct cttccctggt atccattctt tgttgttttt ttttcagacg   180
gagtcttgct ctgtcgccca ggctggagtg cagtggtgcg atcttggctc actgcaagct   240
ctgcctcctg ggttcatgcc attctcctgc ctcagcttcc cgagtagctg ggactacagg   300
cccccgccac cacgcctggc taattttttg tatttttag tagagacggg gtttcaccgt    360
gttagccagg acgatcttga tctcctgacc tcgtgatccg cctgcgtcgg cctcccaaag   420
tgctgggatt acaggcgtga gccaccgtgc ccggcctctg ttcttataag tagtcatttt   480 caccccttgaa aatgtgttgc acaaagatga aaatataatt tccagagaaa tggtatttgc   540
attctgacag tttcttagga aagaaggatg gagtgccaaa attttaatat ggaataagga   600
agaccaactt agatgcaaaa agggcaagag ctttcctgtg actccttagc ttaagttggc   660
tgttgggtta attagttctg tggtttagct gctactgaga ggctactgta gacactggga   720
ctgggataaa gaggtacaag agttcagtgt cttccttaa gatagtggct ctcaattcta    780
tcagtacatg aaatcatgat gctcagggct cctccccaga ccaactgaat aaaaaaacct   840
ggaagtggag cctagacatc tgtattaaaa tgaaattccc tagattctaa tacacactta   900
aggttgagaa ccattcctta acagctaagt gagaattaaa aatacgtaca ttaattgctg   960
tagacatagc agaatatgat tagctctatg atgagtgata gaaattatgg cccaggagtt  1020
ggaaggcttt taattaatag gagccattag gagagactac atcaaggagg ggaattttga  1080
gctggtatat cttcacaggt ggaaagcaga gagtccacta ggccagggaa tgaatgctgt  1140 gagggggaatc tccggagatt tggaagacta ttttgattgg agtgtggtgg aagtaaagat  1200
ggactggtag gctgcagcca gaatgtggac agtctctcgt gtcagactaa ggaattttag  1260
ctttactctg caggtcgtgg ggaggcattc aggatttctg atgagtgaaa tggcaatgct  1320
gaatctttga agattgatcc aatgggagtg atggataggc agtttgaata aaagcaggca  1380
agaacttgag gaaatgaaga ccaattggga agctactctc atggtccaga tgtggggtca  1440
taatgttctg agcgaggcaa atagccgtgg aattaaaaat gataaacatt tgcgtagtat  1500
tttcatagtc agttccttgcc catatctcat ttaaacctca cactgacctt gtggtctttc  1560
cttccatact ttacaaatga aggaactgat gttcagagag aagctgttgt aaaggaacct  1620
tatagaaaat ggagggggcct gattggatga tgaccaatca gtaataggaa attaaagggt  1680
gcattggagg tgttggattg ggtgtgaaga tggtagaatt cctcagtggc taaccatgtc  1740
cagtcaccgg ccgtgctgtc tgagagccac ttcatgctgt tcatgtgact cttcttgcct  1800
ctgtccttta atatgcagtt atttatttat tattattatt attattatta ttgagacgga  1860
```

-continued

| | |
|---|---|
| gtttcgctct cgttgcccag gctggagtgc aatggtgcga tctcggctca ctgaaacttc | 1920 |
| cacctcccag gttcaagcga ttctcctgcc tcagcctccc gagtagctgg gattacaggc | 1980 |
| acctgccacc atgtccagct aattttttgt attttagta gagacggggt ttcaccatgt | 2040 |
| tggccaggct cgtctcaaac tcgtgacctc aggtgatcca cctgcctcgg cctcccaaag | 2100 |
| tgctgggatt acaggcgtga gccaccacgc tcagcctatt tattattatt tttgagacga | 2160 |
| agtcttgctc tgtcacccag gctggagtgc agtggtgctg tctggctcac tccacgctcc | 2220 |
| acctcccagg ttcaagtgat tctcttgcct cagcctcctg agtagctggg attacaggca | 2280 |
| tgcgccacca tgcccagcta attttgtta ttttagtaaa gatgaggttt tgctatgttg | 2340 |
| gccaggctgc tcttgaactc ctcacctaaa gtgatctgcc caaagtgctg ggataacagg | 2400 |
| cgtgagccac tgtgcccagc cacagttact tctttaaagg catagtggag gcaagagaag | 2460 |
| gagaggctgt tgttaattca acttgtctca aatatgaatc ttcaagcctt ttttgaatgt | 2520 |
| ctttgggttt tcagatagtt aaattgtgtt gaattttaaa aggctcagtc taggtatgaa | 2580 |
| tagtctggag ttaaagggct gagactttct tatccaggtg gactctgccc tgagcaggtt | 2640 |
| aactatgact ggtaggtttc catttctctt gtggtggaga caggagccat agggaagaga | 2700 |
| actctggagc atggtagtgt agacaccaga gaacatccct gtggcactgg taactaggat | 2760 |
| gcttcattga gattacatcc ttatcagagc tggagtatga atcatatcca ccaccatgct | 2820 |
| aattcatttt gttcatgagt tggctgtgtc tgtaaggtca tctgtttgt gaaccaagat | 2880 |
| cctgaagcaa ttcaaatgcc agtgtaaatc agccacacag gtgacgaaat gtgcttttcc | 2940 |
| atatgagata cttgttccct gcaatcaaat agtaggagtg caccagaaag ctaagggtac | 3000 |
| taggaggtaa aaaggaatga atcatcatca tgaagaacct tgattagatt tttctcatga | 3060 |
| aatgatgaga tgtggaggag caggatggaa actggaaaag gagaggagat tgaattttg | 3120 |
| tgccccagg | 3129 |

<210> SEQ ID NO 10
<211> LENGTH: 1004
<212> TYPE: DNA
<213> ORGANISM: Homo sapiens

<400> SEQUENCE: 10

| | |
|---|---|
| gaaattatgg cccaggagtt ggaaggcttt taattaatag gagccattag gagagactac | 60 |
| atcaaggagg ggaattttga gctggtatat cttcacaggt ggaaagcaga gagtccacta | 120 |
| ggccagggaa tgaatgctgt gaggggaatc tccggagatt tggaagacta ttttgattgg | 180 |
| agtgtggtgg aagtaaagat ggactggtag gctgcagcca gaatgtggac agtctctcgt | 240 |
| gtcagactaa ggaattttag ctttactctg caggtcgtgg ggaggcattc aggatttctg | 300 |
| atgagtgaaa tggcaatgct gaatctttga agattgatcc aatgggagtg atggataggc | 360 |
| agtttgaata aaagcaggca agaacttgag gaaatgaaga ccaattggga agctactctc | 420 |
| atggtccaga tgtggggtca taatgttctg agcgaggcaa atagccgtgg aattaaaaat | 480 |
| gataaacatt tgcgtagtat tttcatagtc agttcttgcc catatctcat ttaaacctca | 540 |
| cactgacctt gtggtctttc cttccatact ttacaaatga aggaactgat gttcagagag | 600 |
| aagctgttgt aaaggaacct tatagaaaat ggaggggcct gattggatga tgaccaatca | 660 |
| gtaataggaa attaaagggt gcattggagg tgttggattg ggtgtgaaga tggtagaatt | 720 |
| cctcagtggc taaccgtgtc cagtcaccgg ccgtgctgtc tgagagccac ttcatgctgt | 780 |
| tcatgtgact cttcttgcct ctgtccttta atatgcagtt atttatttat tattattatt | 840 |

```
attattatta ttgagacgga gtttcgctct cgttgcccag gctggagtgc aatggtgcga    900
tctcggctca ctgaaacttc cacctcccag gttcaagcga ttctcctgcc tcagcctccc    960
gagtagctgg gattacaggc acctgccacc atgtccagct aatt                     1004

<210> SEQ ID NO 11
<211> LENGTH: 34
<212> TYPE: DNA
<213> ORGANISM: Artificial Sequence
<220> FEATURE:
<223> OTHER INFORMATION: F1-primer

<400> SEQUENCE: 11
ggggtacccc tagaactgca tataagtcct gccc                                 34

<210> SEQ ID NO 12
<211> LENGTH: 35
<212> TYPE: DNA
<213> ORGANISM: Artificial Sequence
<220> FEATURE:
<223> OTHER INFORMATION: F2-primer

<400> SEQUENCE: 12
ggggtacccc gaaattatgg cccaggagtt ggaag                                35

<210> SEQ ID NO 13
<211> LENGTH: 35
<212> TYPE: DNA
<213> ORGANISM: Artificial Sequence
<220> FEATURE:
<223> OTHER INFORMATION: F3-primer

<400> SEQUENCE: 13
ggggtacccc aattttttgt attttagta gagac                                 35

<210> SEQ ID NO 14
<211> LENGTH: 35
<212> TYPE: DNA
<213> ORGANISM: Artificial Sequence
<220> FEATURE:
<223> OTHER INFORMATION: R1-primer

<400> SEQUENCE: 14
gaagatcttc tatcactcat catagagcta atcat                                35

<210> SEQ ID NO 15
<211> LENGTH: 34
<212> TYPE: DNA
<213> ORGANISM: Artificial Sequence
<220> FEATURE:
<223> OTHER INFORMATION: R2-primer

<400> SEQUENCE: 15
gaagatcttc aattagctgg acatggtggc aggt                                 34

<210> SEQ ID NO 16
<211> LENGTH: 35
<212> TYPE: DNA
<213> ORGANISM: Artificial Sequence
<220> FEATURE:
<223> OTHER INFORMATION: R3-primer

<400> SEQUENCE: 16
gaagatcttc cctggggcac aaaaattcaa tctcc                                35
```

PROMOTER

This application is a continuation-in-part of U.S. patent application Ser. No. 09/735,103, filed on Dec. 12, 2000, now abandoned which is a continuation-in-part of, and claims priority from, U.S. patent application Ser. No. 09/142,529, filed on Aug. 12, 1999, now U.S. Pat. No. 6,225,459, which, in turn, is a 371 of international patent application serial number PCT/JP97/00741, filed on Mar. 10, 1997, which, in turn, claims priority from Japanese patent application serial number JP 8/54294, filed on Mar. 12, 1996, the disclosures of which are hereby incorporated by reference.

TECHNICAL FIELD

The present invention relates to the field of genetic engineering, particularly the field of gene therapy.

BACKGROUND ART

Gene therapy attempts to treat diseases caused by congenital or acquired genetic defects, namely gene disorders, by substituting or supplementing defective genes with normal genes. Although various treatment methods for gene therapy have been investigated, only a very limited number of the methods to date have met with success, including the treatment of adenosine deaminase (ADA) deficiency. This is mainly because the methods for efficiently introducing a therapeutic gene into target cells and the methods for expressing an introduced gene in the cell have not yet been established. So far, liposomes, HVJ-liposomes, retroviruses, and the like have been employed as carriers introducing the therapeutic gene into target cells. However, none of them are satisfactory in gene introduction efficiency. Various attempts have been made to increase the expression efficiency of the introduced gene, by, for example, improving the promoter. However, in each case the expression efficiency of the desired gene was still poor, and the quantity of the gene product was insufficient to afford gene therapy. Thus, in the field of gene therapy, a vector that enables a high level expression of a therapeutic gene in a variety of target cells has been sought.

In the field of hematology, Tec tyrosine kinase, a protein thought to participate in the proliferation of hematopoietic stem cells, is highly expressed in mouse liver, and is also expressed in the kidney, heart, and ovary (Oncogene, 5, 1781–1786 (1990)). In humans, Tec tyrosine kinase is highly expressed in a wide range of blood and lymphoid cells (LEUKEMIA, 8, 1663–1672 (1994)). However, human Tec promoter has not been reported so far, and its function has only been predicted from the study on the corresponding mouse sequence.

DISCLOSURE OF THE INVENTION

An objective of the present invention is to provide a vector having incorporated within it a promoter functioning efficiently in a wide variety of blood and lymphoid cells, and the cells of organs such as the liver, thereby providing a gene therapy technique targeting blood and lymphoid cells.

The present inventors noted that Tec tyrosine kinase, a protein thought to participate in the proliferation of hematopoietic stem cells, is highly expressed in a wide variety of blood cells, lymphoid cells, and the cells of organs such as the liver. The inventors isolated the promoter of Tectyrosine kinase from a mouse genomic DNA, constructed a vector with the promoter incorporated within it ligated an exogenous gene adjacently downstream of it, and attempted to express the exogenous gene in the cells. As a result, they found that the exogenous gene was actually expressed in the cells at a high level. However, in view of species specificity and safety, human Tec promoter appears to be more useful than mouse Tec promoter when used in gene therapy for treating humans. Thus, a human genomic library was screened for Tec promoter, and a DNA fragment of 3,129 bp in length was isolated and sequenced (FIG. 3). Thus, the present invention relates to:

(1) a DNA comprising the nucleotide sequence of SEQ ID NO:10 and having promoter activity;
(2) an expression vector comprising the DNA of (1); and
(3) a cell carrying the expression vector of (2).

In the present invention, "a DNA having promoter activity" means a DNA having activity to induce the transcription of a DNA region adjacent to the DNA. The present invention includes a DNA containing a part or whole of the nucleotide sequence of SEQ ID NO:1, and having promoter activity as well as the DNA having the nucleotide sequence of SEQ ID NO:1. Preferably, the DNA of the present invention has a length of at least about 50 bp, more preferably at least about 100 bp, even more preferably at least about 200 bp, and most preferably at least about 300 bp. The present invention also includes a DNA containing a part or whole of the nucleotide sequence of SEQ ID NO: 9, and having promoter activity as well as the DNA having the nucleotide sequence of SEQ ID NO: 9. Preferably, the DNA of the present invention has a length of at least about 50 bp, preferably at least about 100 bp, more preferably at least about 150 bp, even more preferably at least about 200 bp, and most preferably at least about 300 bp, for example, at least about 400 bp or at least about 500 bp. The present invention also relates to at least 1 kb sequence located in between approximately 1 kb to 2 kb upstream from the 3' terminus of the sequence of SEQ ID NO: 9. The inventors have studied the promoter activity of this sequence, using a reporter assay in which luciferase luminescence is measured.

According to the present invention, any vector for use in gene introduction can basically be used as a "vector" into which the DNA having promoter activity is to be introduced. Particularly in gene therapy, viral vectors, such as retrovirus vectors, adenovirus vectors, or adeno associated virus vectors, and non-viral vectors such as liposomes should be used.

Any cell is included in the "cell carrying the expression vector" of the present invention. Cells that have been confirmed to actually express the Tec tyrosine kinase gene, including blood cells and lymphoid cells, such as hematopoietic stem cells, myeloid cells, B cells, and T cells, and the cells of internal organs such as the liver, kidney, heart, and ovary should be used.

One skilled in the art may be able to prepare and identify a DNA containing a part of the nucleotide sequence of SEQ ID NO: 9, and having promoter activity by digestion with exonucleases such as ExoIII and Bal31 or restriction enzymes and by examining the promoter activity of the DNA as follows. The DNA is ligated upstream of a reporter gene, such as luciferase gene, on an expression vector containing no promoter, for example, pUC00Luc, etc. By introducing the vector into cells highly expressing the Tec mRNA such as BA/F3 cells, test cells for assays of reporter gene activity are prepared. After cultured, the cells are harvested and subjected to the assays. For example, the assays for luciferase can be performed according to the ordinary method (the method according to the manual of "Luciferase Assay System" (Promega)). As a control, cells into which the same expression vector containing no promoter as mentioned above has been introduced are used without ligating any DNA upstream of the reporter gene. If the expression level of the reporter gene is significantly higher in the test cells than in the control cells, it is confirmed that the DNA has promoter activity.

BRIEF DESCRIPTION OF THE DRAWINGS

FIG. 1 shows the nucleotide sequence of the 5' flanking region of a mouse Tec gene according to the present invention (SEQ ID NO: 1).

FIG. 3 shows the entire nucleotide sequence of the 3,129 bp fragment containing the human Tec promoter according to the present invention (SEQ ID NO: 9).

FIG. 4 shows the nucleotide sequences of the primer (SEQ ID NO: 11–16) and combinations of the primers used to generate the PCR fragments corresponding to whole or part of the 3,129 bp fragment. FIG. 4 also shows the portions amplified with each primer set listed above.

BEST MODE FOR IMPLEMENTING THE INVENTION

Figure 2:
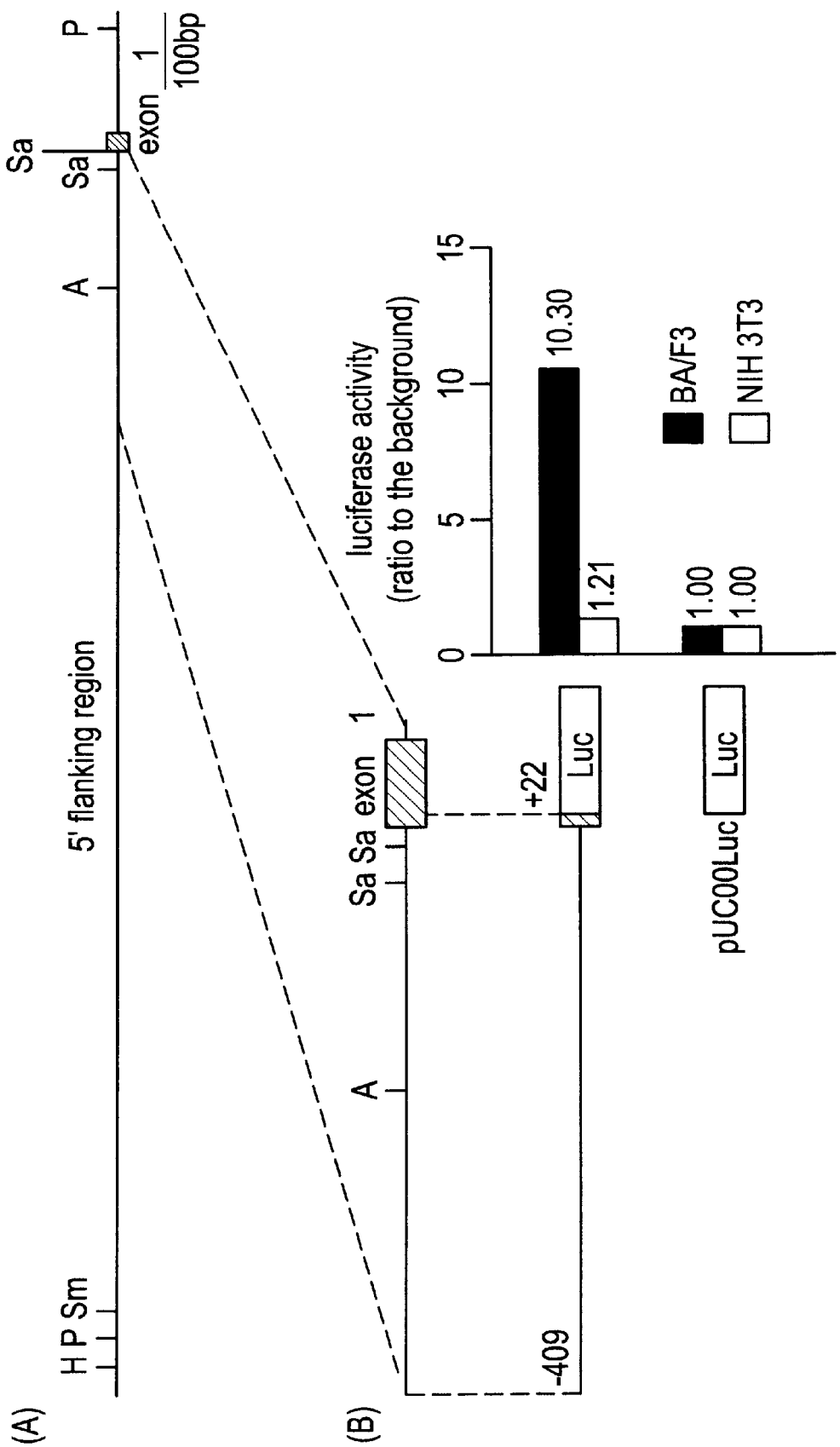
FIG. 2 shows the luciferase activity of BA/F3 and NIH 3T3 cells, into which pUC00Luc, having incorporated within it a 5' flanking region fragment of a mouse Tec gene and a luciferase gene adjacently linked thereto, was introduced. As a control pUC00Luc, which does not contain a 5' flanking region fragment, was used.

The following examples will be given to illustrate the present invention in detail, but are not construed to limit the scope of the present invention.

EXAMPLE 1

Construction of the Mouse Genomic Library

A high molecular weight genomic DNA was extracted from BA/F3 cells. The DNA was partially digested with Sau3AI (Takara Shuzo), and dephosphorylated with bacterial alkaline phosphatase (BAP; Takara Shuzo). The resulting DNA fragments were incorporated into the BamHI-digested EMBL3 vector (Stratagene), and in vitro packaged using "Gigapack Gold extracts" (Stratagene). The recombinant phage thus obtained was used to infect the *E. coli* LE392 strain.

EXAMPLE 2

Screening of the Mouse Tec Promoter

In order to obtain the promoter region from a mouse Tec gene, a screening probe was prepared by PCR as follows. First, a primer corresponding to the 15th through the 32nd nucleotides, and a primer corresponding to the 122nd through the 141st nucleotides of the Tec cDNA (SEQ ID NO:2; Oncogene, 8, 417–424 (1993)) were synthesized, and used to amplify the 5' region of the mouse Tec cDNA. The amplification by PCR was performed using 10 ng of the mouse Tec cDNA as a template. The PCR product (approximately 127 bp) was thus purified, radioactively labeled with $^{32}$P, and used as a probe to screen the mouse genomic library by performing hybridization in a solution containing 5×SSC (1×SSC: 150 mM NaCl, 15 mM Na-Citrate), 5×Denhardt's solution (1 mg/ml polyvinylpyrrolidone, 1 mg/ml bovine serum albumin, 1 mg/ml Ficoll), 0.5% SDS, 100 ng/ml salmon sperm DNA, and the $^{32}$P-labeled PCR fragment, at 65° C. overnight. The filters were washed twice in 2×SSC/0.1% SDS at 55° C. for 20 minutes, and twice in 0.2×SSC/0.1% SDS at 55° C. for 20 minutes. The signal was detected by exposing the filters onto "Kodak XAR Films" (Kodak) with intensifying screens for 24 to 72 hours at −80° C. As a result, 13 positive clones were obtained. The secondary screening was done for these positive clones using as a probe the nucleotide corresponding to the Tec cDNA positions 15 to 39 that was radioactively labeled in the same manner as above by performing hybridization under the same conditions as above except that the temperature was 55° C., and the washing was done twice in 2×SSC/0.1% SDS at 55° C. for 20 minutes each time. Consequently, two positive clones were obtained.

EXAMPLE 3

Analysis of the Transcription Initiation Site of the Mouse Tec Gene

In order to analyze the transcription initiation site of the mouse Tec gene, RACE-PCR was performed as follows. First, 5 µg of mRNA was extracted from BA/F3 cells and annealing was performed using the oligonucleotide, 5'-TTAGCATCATGAACAAC-3' (Primer 1; SEQ ID NO: 3), which corresponds to the nucleotide positions 358 through 374 of the Tec cDNA (hereinafter applying the same nucleotide positions as in SEQ ID NO:2) as an antisense primer against this mRNA. The annealing product was subjected to cDNA synthesis and d(A) tailing. The primary PCR was then performed using the above primer as the template and using as primers the oligonucleotide, 5'-CCTTACCCTCATAGTAGCTCA-3' (Primer 2; SEQ ID NO: 4), which corresponds to the nucleotide positions 227 through 247 of the Tec cDNA, and the oligonucleotide, 5'-GACTCGAGTCGACATCGATTTTTTTTTTTTTTTT-3' (Primer 3; SEQ ID NO:5). The primary PCR was done for 40 cycles of 94° C. for 40 sec, 55° C. for 2 min, and 72° C. for 3 min. In addition, the secondary PCR was performed under the same conditions as the primary PCR, except that the oligonucleotide, 5'-TCAACACTATCCTAGAAGAG-3' (Primer 4; SEQ ID NO: 6), which corresponds to the nucleotide positions 122 through 141 of the Tec cDNA, and the oligonucleotide, 5'-GACTCGAGTCGACATCG-3 (SEQ ID NO: 7), were used instead of Primer 2 and Primer 3. As a negative control for this experiment, a RACE-PCR was done without the reverse transcriptase. Next, the PCR products were electrophoresed on agarose, and stained with ethidium bromide (EtBr). As a result, a PCR product of approximately 250 bp was detected only when the RACE-PCR was performed with the reverse transcriptase. In order to confirm that the desired region had been amplified, the PCR products were transferred onto a nitrocellulose membrane after the agarose electrophoresis was hybridizated against this membrane using the $^{32}$P-labeled oligonucleotide, 5'-GCAGTTTGGACGTCGCTCTGTCTTG-3' (SEQ ID NO: 8), which corresponds to the nucleotide positions 15 through 39 of the Tec cDNA. The result showed that the PCR products contained most of the 5' region of the Tec cDNA, and that the Tec mRNA was accurately amplified by RACE-PCR.

When the 5'-side sequences of the thus-obtained DNA fragments were determined, an identical sequence (5'-CGCAGTTTGG . . . )(SEQ ID NO:1) after polyT sequence was found in seven out of eight clones, and therefore, the 5' terminal "C" of the sequence was identified as the transcription initiation site. The transcription initiation site is indicated by arrows in FIG. 1.

EXAMPLE 4
Analysis of the 5' Flanking Region of the Mouse Tec Gene

The nucleotide sequence of the 5' flanking region of the mouse Tec gene was determined by the dideoxy method. The sequence thus determined is shown in FIG. 1, and SEQ ID NO:1. The result indicated that there is no sequence, which is clearly identified as a TATA box or a CAAT box within the 5' flanking region. Instead, there was a GATA site and a consensus sequence for the SP-1 factor-binding site (FIG. 1).

EXAMPLE 5
Analysis of Promoter Activity of the 5' Flanking Region of the Mouse Tec Gene A fragment consisting of a part of the mouse Tec gene 5' flanking region and exon 1 (the region from −409 to +22) was incorporated into an expression vector containing no promoter, pUC00Luc, and introduced into BA/F3 cells, which highly express the Tec mRNA, and into NIH 3T3 cells, which do not express the Tec mRNA, as follows. First, $1 \times 10^7$ cells in their growth phase were washed with PBS, and incubated with 500 µg of DEAE dextran (Pharmacia) and 10 µg of a reporter plasmid DNA at room temperature for 25 minutes. The cells were then cultured in the medium containing 100 µM chloroquine at 37° C. for 1 hour. The culturing was done in 5% carbon dioxide. The cells were washed with PBS, incubated in the culture medium for 48 hours, and harvested for the luciferase analysis using the "Luciferase Assay System" (Promega). As a control in the above experiment, the cells into which pUC00Luc containing no 5' region fragment had been introduced were used. The luciferase activity assay was performed according to the ordinary method (the method according to the manual of "Luciferase Assay System" (Promega)).

From the results obtained, BA/F3 cells showed 10 times higher luciferase activity than NIH 3T3 cells when pUC00Luc containing the 5' region fragment was introduced into these cells (FIG. 2). In contrast, in the control experiment, no luciferase activity was detected in any cell line (FIG. 2). Consequently, it was revealed that the 5' flanking region of the mouse Tec gene possesses promoter activity.

It is acknowledged that one skilled in the art may be able to prepare and identify a shorter DNA fragment by preparing a shorter promoter having nucleotide sequence of SEQ ID NO:1 by digestion with exonucleases such as ExoIII and Bal31 or restriction enzymes and examining the promoter activity of the DNA fragments according to the method described in this Example.

EXAMPLE 6
Screening of the Human Tec Promoter

In order to obtain the promoter region from a human Tec tyrosine kinase gene, a screening probe was prepared by PCR as follows. First, a primer corresponding to the 71st through the 95th nucleotides, and a primer corresponding to the 229th through the 254th nucleotides of the human Tec cDNA (Gen Bank Accession No. NM_003215) were synthesized, and used to amplify the 5' region of the human Tec cDNA. The amplification by PCR was performed using as a template the human Tec cDNA purified from a human genomic library "Whole Blood Lambda Genomic Library" (Stratagene). It was confirmed by sequencing that the PCR product obtained (184 bp) had the sequence of the desired Tec gene. Then, the amplification by PCR was performed using the PCR product as a template and using DIG DNA Labeling mix (Roche Diagnostics) labeled with digoxigenin (DIG), thereby obtaining a DIG-labeled PCR product. This DIG-labeled PCR product was used as a probe to screen $2 \times 10^5$ pfu human genomic library. The phages were plated at a density of 4000 pfu per 9-cm plate and were blotted and fixed onto membrane filters "Hybond-N$^+$" (Amersham Pharmacia). Hybridization was performed in a solution containing 50% formamide, 5×SSC (1×SSC: 150 mM NaCl, 15 mM Na-Citrate), 5×Denhardt's solution (1 mg/ml polyvinylpyrrolidone, 1 mg/ml bovine serum albumin, 1 mg/ml Ficoll), 0.5% SDS, 100 mg/ml salmon sperm DNA, and the DIG-labeled PCR fragment, at 42° C. overnight. The filters were washed in 2×SSC/0.1% SDS at 65° C. for 20 minutes, then in 0.2×SSC/0.1% SDS at 65° C. for 20 minutes, and finally in 0.1×SSC/0.1% SDS at 65° C. for 20 minutes. The signal on the washed filters was detected by immunostaining. Immunostaining was performed as follows. The filters were first blocked with 5% skim milk in TBST (10 mM Tris-HCl, pH 9.5, 150 mM NaCl, 0.05% Tween20) and then incubated in a solution of anti-DIG antibody conjugated with alkaline phosphatase "Anti-Digoxigenin-AP Fab fragments" (Roche Diagnostics) at a 1:5000 dilution in TBST at room temperature for 30 minutes. The filters were washed three times in TBST at room temperature for 10 minutes and reacted with detection solution containing the substrates of alkaline phosphatase (NBT and BCIP). As a result, one positive clone was obtained. The secondary and tertiary screening was done until the positive clone was isolated as a single plaque. The phage isolated as a single plaque was amplified by plate lysate method (Sambrook, J. et al., eds. 1989: Molecular cloning: a laboratory manual, 2nd ed., Cold Spring Harbor Laboratory Press). From the amplified phage solution, DNA was extracted with a DNA extraction kit "QIAGEN Lambda kit" (QIAGEN). The insert DNA excised from the phage vector thus extracted was revealed to be about 17 kbp long. The insert DNA was cut with a restriction enzyme into short fragments and subcloned into a cloning vector. The fragment containing the promoter region was sequenced. As a result, the sequence of 3,129 bp fragment expected to contain the human Tec promoter region was determined (SEQ ID NO: 9).

EXAMPLE 7
Analysis of Promoter Activity of the Human Tec Promoter

To define the region having promoter activity in the 3,129 bp sequence obtained in the Example 6, fragments of various lengths were prepared using PCR. The fragments were subcloned into reporter vector pGL3-Basic Vector (Promega), which encodes firefly luciferase, and then transfected into cells (Ba/F3 and 293T cells) by means of electroporation or lipofection. The transfected cells were subjected to a reporter assay to determine the promoter activity by using a commercially available kit (Dual-Luciferase Reporter Assay System: Promega).

Preparation of the PCR Fragments

Six oligonucleotides, F1, F2, F3, R1, R2 and R3 (SEQ ID NOs: 11, 12, 13, 14, 15 and 16, respectively), were synthesized (FIG. 4) initially and used as primers. Primers F1, F2, F3, R1, R2 and R3 bind to nucleotide positions 1–25, 1001–1025, 2001–2025, 1000–976, 2004–1981 and 3129–3105 of the 3,129 bp sequence of the human Tec promoter, respectively. F and R denote forward and reverse primers, respectively. The KpnI and BglII restriction enzymes recognition sequences are added to the 5' ends of the F and R primers, respectively, to facilitate subcloning of the amplified fragments into the plasmid by using the restriction sites. Combination of the six primers allowed generation of six fragments of different lengths (FIG. 4). PCR reaction was performed under the following conditions: 30 seconds at 96° C., 35 cycles of 15 seconds at 96° C., 45 seconds at 55° C. and 2.5 minutes at 72° C., and 4° C.

Cloning of the PCR Fragments

The six PCR fragments thus generated were cleaved with restriction enzymes KpnI and BglII, and ligated between the KpnI and BglII sites of reporter plasmid pGL 3-Basic Vector (Promega) pretreated with KpnI and BglII. The ligated samples were used to transform competent cells DH5-α (TOYOBO), which were plated on the medium containing ampicillin for selecting the transformants. Colonies of the transformants were picked up and cultured in a small volume, and subjected to plasmid DNA extraction using a commercially available kit (QIAprep Spin mini prep kit; QIAGEN). The DNA thus obtained were sequenced using automatic DNA sequencer (Applied Biosystems) for confirmation of the nucleotide sequence. One clone for each construct was selected, which harbored a plasmid having no mutation in the sequence of interest. The selected clones were cultured in a large volume and subjected to extraction of plasmid DNA by a commercially available kit (QIAGEN plasmid midi kit; QIAGEN). The plasmids carrying fragments 1 to 6 were designated hTec 1 to 6 (FIG. 4), respectively and their DNA were used for further investigation.

Luciferase Assay

Ba/F3 and 293T cells were used for transfection. Since Ba/F3 cell is suspension cell line and difficult to be transfected, electroporation was used to transfect this cell line. Electroporation was performed, using Gene Pulser (BioRad) as an electroporator, on $5 \times 10^6$ cells in the cuvette in which two electrodes are placed 0.4 cm apart and under the pulse of 950 μF and 200V. Transfection of 293T cells were carried out using a kit utilizing lipofection (Lipofect Amine Plus; Invitrogen).

Nine constructs in total, i.e. mouse Tec gene with mouse Tec promoter, pGL3-control vector carrying SV40 promoter for the positive control, and promoter-less pGL3-control vector for the negative control, as well as hTecs 1 to 6, were introduced into the cells. A plasmid vector encoding Renilla luciferase (pRL-TK vector; Promega), to which a luminescence reagent different from that for firefly luciferase is applied, was co-transfected at a ratio of pGL3: pRL=20:1. This was intended to serve as an index of internal control to prevent errors that occur from difference in transfection efficiency or number of the cells.

Thirty hours after the transfection, the cells were measured for their luminescence emitted from firefly and Renilla transferases through luminometer using the Dual-Luciferase Reporter Assay System kit (Promega).

Figure 6:
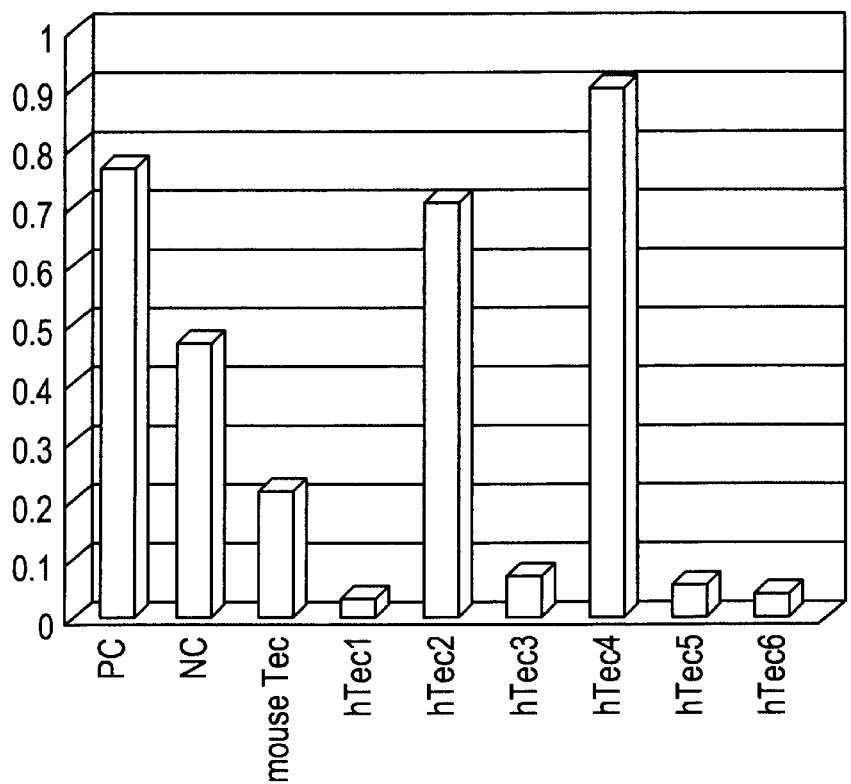
FIG. 6 shows the promoter activity of the whole or part of the 3,129 bp fragment in human 293T cells.

The luciferase assay showed that the 3,129 bp sequence of human Tec promoter has promoter activity (FIG. 6). Comparison of the activity of clones 1 to 6 suggests that the active center resides in the approximately 1 kb fragment of hTec4. The fact that the entire fragment of about 3 kbp showed little activity can be accounted for by the presence of the 1 kb region at the 3' terminus of the fragment which suppresses the promoter activity. These results enabled the inventors to demonstrate the promoter function of the sequence and to define the promoter region of the human Tec promoter on a kp basis.

Figure 5:
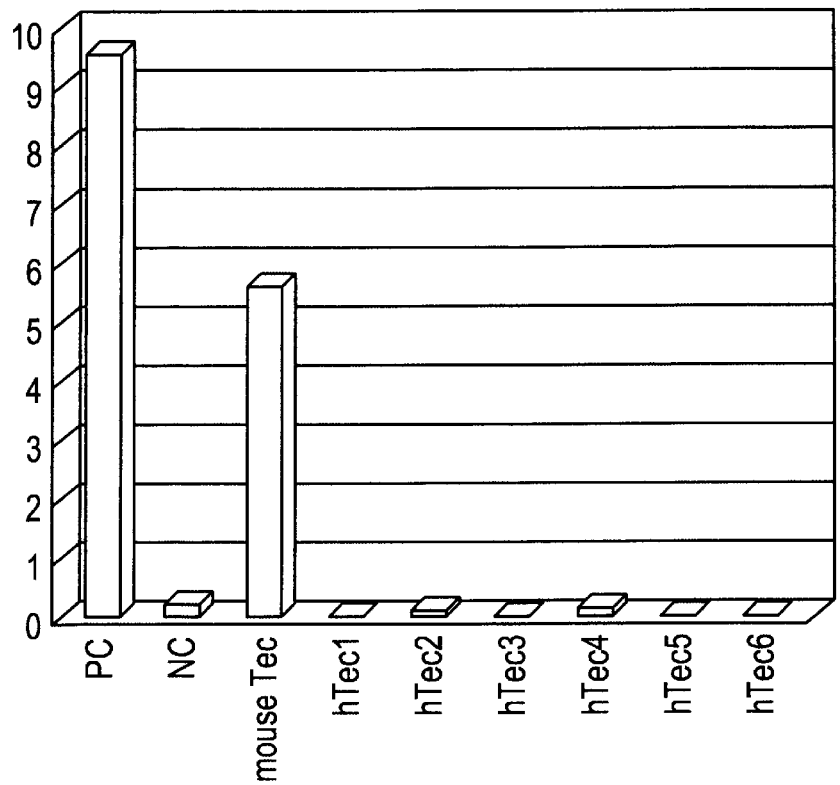
FIG. 5 shows the promoter activity of the whole or part of the 3,129 bp fragment in mouse Ba/F3 cells.

Interestingly, the promoter activity was different for the cell lines used (FIGS. 5 and 6). Fa/F3 cells are derived from mouse blood cells and express mouse Tec tyrosine kinase. On the other hand, 293T cells are derived from human kidney and are thought to express human Tec kinase. The species-specific activity of the human Tec promoter was suggested by the fact the human Tec promoter showed little activity in the mouse Ba/F3 cells and is active in the human 293T cells. Accordingly the human Tec promoter is expected to serve as a promoter used in the vectors for gene therapy.

Industrial Applicability In the present invention, the promoter of the Tec tyrosine kinase, which is highly expressed in a wide variety of blood cells, lymphoid cells, and the cells of organs such as the liver, was isolated, and its structure was clarified. Furthermore, the present invention enables the production of a vector having incorporated within it the promoter and a high level expression of an exogenous gene in hematopoietic stem cells, liver cells, and the like. A major breakthrough is expected particularly in the field of gene therapy targeting blood cells or the cells of organs such as the liver.

What is claimed is:

1. An isolated DNA having promoter activity and comprising the nucleotide sequence of SEQ ID NO: 10.

2. An expression vector comprising the isolated DNA of claim 1.

3. An isolated cell comprising the expression vector of claim 2.

* * * * *

UNITED STATES PATENT AND TRADEMARK OFFICE
CERTIFICATE OF CORRECTION

PATENT NO.    : 6,500,943 B2  
DATED         : December 31, 2002  
INVENTOR(S)   : Hiroyuki Mano, Tsuneaki Sakata, Mamoru Hasegawa and Toshiaki Tabata Page 1 of 1

It is certified that error appears in the above-identified patent and that said Letters Patent is hereby corrected as shown below:

Title page,
Item [54], replace "PROMOTER" with -- HUMAN TEC PROMOTER --
Item [73], Assignee, replace "Dnavec" with -- DNAVEC --;
Item [75], Inventors, "Hiroyuki Mano", replace "Utsunomiya" with -- Tochigi --; "Tsuneaki Sakata", replace "Toyonaka" with -- Osaka --; "Mamoru Hasegawa", replace "Tsukuba" with -- Ibaraki --; and "Toshiaki Tabata", replace "Tsukuba" with -- Ibaraki --.

Signed and Sealed this

Tenth Day of August, 2004

JON W. DUDAS
*Acting Director of the United States Patent and Trademark Office*